US008431910B1

(12) United States Patent
Perry

(10) Patent No.: US 8,431,910 B1
(45) Date of Patent: Apr. 30, 2013

(54) AUTO-STERILIZATION OF ELECTRONIC AND HAND HELD DEVICES

(75) Inventor: Matthew Perry, Rochester, MA (US)

(73) Assignee: Lockheed Martin Corporation, Bethesda, MD (US)

( * ) Notice: Subject to any disclaimer, the term of this patent is extended or adjusted under 35 U.S.C. 154(b) by 177 days.

(21) Appl. No.: 12/868,822

(22) Filed: Aug. 26, 2010

(51) Int. Cl.
*A61L 2/10* (2006.01)

(52) U.S. Cl.
USPC ............... 250/455.11; 422/24; 422/186.3; 362/551

(58) Field of Classification Search ............ 422/24; 250/455.11; 362/551, 554, 559
See application file for complete search history.

(56) References Cited

U.S. PATENT DOCUMENTS

| | | | |
|---|---|---|---|
| 6,428,198 B1 * | 8/2002 | Saccomanno et al. | 362/559 |
| 6,524,529 B1 * | 2/2003 | Horton, III | 422/24 |
| 6,766,097 B2 * | 7/2004 | Horton, III | 385/147 |
| 7,598,501 B2 | 10/2009 | Jones | |
| 7,658,321 B1 | 2/2010 | Greco et al. | |
| 7,692,159 B2 | 4/2010 | Lane et al. | |
| 7,744,555 B2 | 6/2010 | DiMauro et al. | |
| 2008/0286145 A1 | 11/2008 | Ratcliffe | |
| 2009/0184268 A1 | 7/2009 | Garcia et al. | |
| 2009/0218512 A1 | 9/2009 | Ranta et al. | |
| 2010/0127189 A1 | 5/2010 | Boyarsky et al. | |
| 2011/0291995 A1 * | 12/2011 | Shr et al. | 345/176 |

OTHER PUBLICATIONS

Philip W. Brickner, MD; Richard L. Vincent, BSc; Melvin First ScD; Edward Nardell, MD; Megan Murrary, MD, MPH, ScD; Will Kaufman, BSc; "The Application of Ultraviolet Germicidal Irradiation to Control Transmission of Airborne Disease: Bioterrorism Countermeasure", Public Health Reports, Mar.-Apr. 2003/ vol. 118, pp. 99-114.

Yang Yu, Ning Liu, Angelo Sassaroli, and Sergio Fantini, "Design and Performance of a Near-Infrared, Spectral Imaging System for Optical Mammography"; Tufts University, Department of Biomedical Engineering, 2007.

* cited by examiner

*Primary Examiner* — Sean E Conley
(74) *Attorney, Agent, or Firm* — Howard IP Law Group, PC

(57) ABSTRACT

An arrangement is disclosed for automatically sterilizing hand-held electronic devices. The arrangement includes a source of Ultraviolet (UV) light, as well as one or more fiber-optic filaments for transmitting the UV light for output at one or more locations on the hand-held electronic device. Software is provided to enable a user to pre-program a desired sanitization schedule for one or more portions of the device. In one embodiment, a UV protective cover is provided to protect UV-sensitive portions of the hand-held electronic device.

13 Claims, 7 Drawing Sheets

AUTO-STERILIZATION OF ELECTRONIC AND HAND HELD DEVICES

FIELD OF THE DISCLOSURE

The disclosure generally relates to the field of surface sterilization, and more particularly, to sterilization of electronic devices using ultraviolet light.

BACKGROUND

One of the most common places to find infectious bacteria and viruses is the keyboard, second to the only the phone. Surprisingly work station desks contain the highest traces of the following bacteria and viruses: Bacteriophage (*E. Coli*), Infectious Hepatitis, Influenza, *Staphylococcus Aureus* (MRSA), Streptococcus (Strep Throat), *Shigella Flexneri* (Dysentary), Pinkeye (Viral & Bacterial), *Salmonella Typhosa* (Typhoid Fever), *Leptospira* (Jaundice), and *Corynebacterium* (Family causes Strep, Meningitis, Scarlet Fever).

Sterilization of electronic device is often performed by spraying chemicals directly on to the surface of the device and allowed to dry for 15 to 20 minutes. The most notable side effects from such sterilization are a sticky film and strong cleanser odor.

Ultraviolet Germicidal Irradiation (UVGI) devices are known. Such devices typically mimic a flashlight or wand that a user can hold over a surface that requires sterilization. The UV light that impinges upon the surface is held long enough to kill bacteria and/or virus residing therein. UVGI systems are also common for use in maintaining air quality in commercial and medical facilities. In such facilities, air is circulated near several UVGI lamps, which sterilizes the air and readies it for re-circulation throughout main air ducts. Similar UVGI systems are used to expose water tanks and sealed rooms to UVGI light. Existing technology utilized in these UVGI systems comprises large UV lamps and massive power supplies and regulators.

As noted, using chemical sterilizers leaves an undesirable residue on surfaces of the device. Shining a UVGI lamp over a device is labor intensive and undesirably requires a user to take periodic action in order to sterilize the device. Large-scale UVGI sterilization systems are too massive to be practically integrated into hand-held device architectures. It would therefore be advantageous to provide a simple to use arrangement for sterilizing electronic devices commonly touched by people that requires neither chemical application nor continuous or periodic user action.

SUMMARY

The disclosed technique focuses on the problem of keeping a sterile work environment, in the office, workplace, field or at home. Regardless of the application the concept is applied to (e.g., military, medical, commercial and space) common electronic devices such as keyboards, cell phones, touch screens, electrical devices in general can contain a staggering amount of bacteria and viruses. The disclosed arrangement addresses the problem of bacteria and viruses, which can linger on devices, by allowing an electrical device to automatically sterilize the surface of the device. With more and more concerns over avian and swine flu there is a need to help minimize the amount of bacteria and viruses passed unknowingly to each other simply by using common electrical devices.

The disclosed arrangement leverages a process referred to as Ultraviolet Germicidal Irradiation (UVGI) to sterilize bacteria and viruses on electronic devices commonly touched by people. UVGI is implemented by means of a miniature UVC source (~280 to 100 nm) combined with UV-passing fiber optics which allow the UV to be broadcast via a string of radiators and/or reflectors. Safe levels of UV radiation are established and controlled such that safe exposure levels are always maintained (e.g., 6000 W sec/cm$^2$ over a daily 8-hour period on unprotected skin or eyes). An additional aspect unique to the disclosed arrangement is the application of a protective UV diffuser placed over the touch screen of the device (e.g., cell phone, computer monitor) so that any sensitive electronics internal to the electronic device are not unintentionally affected by the emitted UV radiation.

The disclosed arrangement incorporates an auto-sterilization function directly into the electronic device. In one exemplary embodiment, the arrangement utilizes a laser and fiber so that the hardware can be packed into small devices. Other arrangements are also considered, such that the light source and how it travels to the reflectors/radiators may vary. For example, UVC cable light emitting diodes or LEDs could be used in lieu of lasers and associated fibers. Coupled with software that can manage the scheduling of sterilization, the arrangement enables a user to establish a routine in which the device can be sterilized on a non-interfering basis, and as often as the user desires (e.g., every day during off hours).

A system for sterilizing electronic devices is disclosed. The system may include a UV radiation source and a distribution fiber coupled to the UV radiation source for transmitting UV radiation to an output end of said distribution fiber. At least one of the UV radiation source and the distribution fiber can be integrated into a structure of an electronic device such that UV radiation output from said output end of said distribution fiber impinges on a surface of said electronic device to sterilize said surface.

A method for sterilizing an electronic device is also disclosed. The method includes providing a UV radiation source and a distribution fiber coupled to the UV radiation source for transmitting UV radiation to an output end of said distribution fiber, where at least one of the UV radiation source and the distribution fiber are integrated into a structure of an electronic device; and outputting UV radiation from said output end of said distribution fiber onto a surface of said electronic device to sterilize said surface.

BRIEF DESCRIPTION OF THE DRAWINGS

The details of the invention, both as to its structure and operation, may be obtained by a review of the accompanying drawings, in which like reference numerals refer to like parts, and in which.

DETAILED DESCRIPTION

Figure 1:
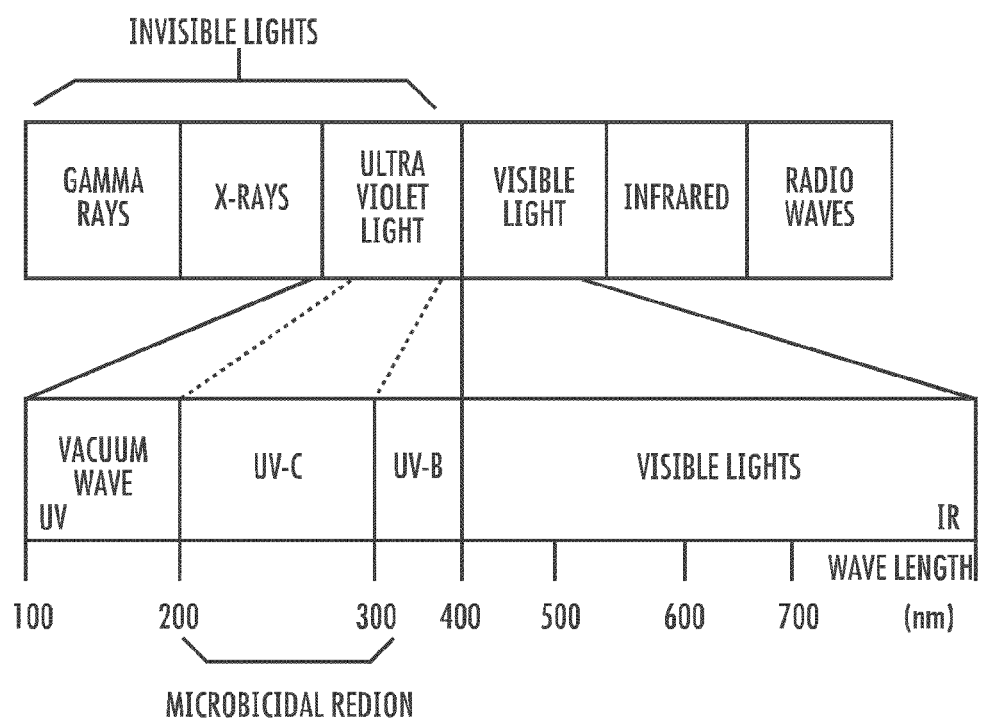
FIG. 1 is a graph showing the region of the UV spectrum that is designated UVC and such light can be used for Ultraviolet Germicidal Irradiation (UVGI)

An arrangement is disclosed for sterilizing electronic devices, including hand held devices, through the use of Ultraviolet Germicidal Irradiation (UVGI). Ultraviolet (UV) light is electromagnetic radiation with wavelengths shorter than visible light. UV light can be separated into various ranges, with short range UV (UVC) considered "germicidal UV." At certain wavelengths UV light is mutagenic to bacteria, viruses and other micro-organisms. At a wavelength of 2,537 Angstroms (254 nm) UV light will break the molecular bonds within micro-organismal DNA, producing thymine dimers in their DNA, thereby destroying them and rendering them harmless or prohibiting growth and reproduction. It is a process similar to the UV effect of longer wavelengths (UVB) such as sunburn or sun glare on humans. Micro-organisms have even less protection from UV and thus cannot survive prolonged exposure to it. FIG. 1 shows the range (in wavelength) of the UVC spectrum, which is from about 200 nm to about 300 nm.

As evident in recent news, a viral pandemic is something that we and future generations are going to have to Cope with for many years to come. With Avian and Swine Flu in the minds of many legislators, it is only a matter of time when laws, rules and processes will be levied on the military, medical and commercial industries regarding the sterilization of public use equipment and electronic devices. This market would consist of an auto-sterilizing capable keyboard, mouse, cell phone and PDA. Additionally, the medical field greatly benefits from sterile equipment and therefore lends itself to being one of the first applications. Finally, this type of functionality can be incorporated into military products (combat system displays, touch screens, etc.). Maintaining a clean environment is important in any confined work space shared with several co-workers (i.e., submarines and other naval vessels where access to resources is limited and keeping equipment clean and sterile is critical while at sea). Each of these applications have unique characteristics, however they all are based around the same core set of technologies.

The disclosed arrangement involves incorporating a UV light source into or onto a surface of any electronic device that is commonly handled by people. For sterilizing a keyboard, UV fiber optic fiber can be routed to several locations within the keyboard. Each fiber couples and directs the UV light in such a way that all surfaces within a 1"-2" distance from the output of the fiber would be sterilized. For a standard keyboard there may be 5 or 6 areas from which light will emanate. Touch screen monitors can benefit from a similar design. The touch screen can be sterilized with UV light emanating from corners of the screen, with a film of light directed over the full screen.

Figure 2:
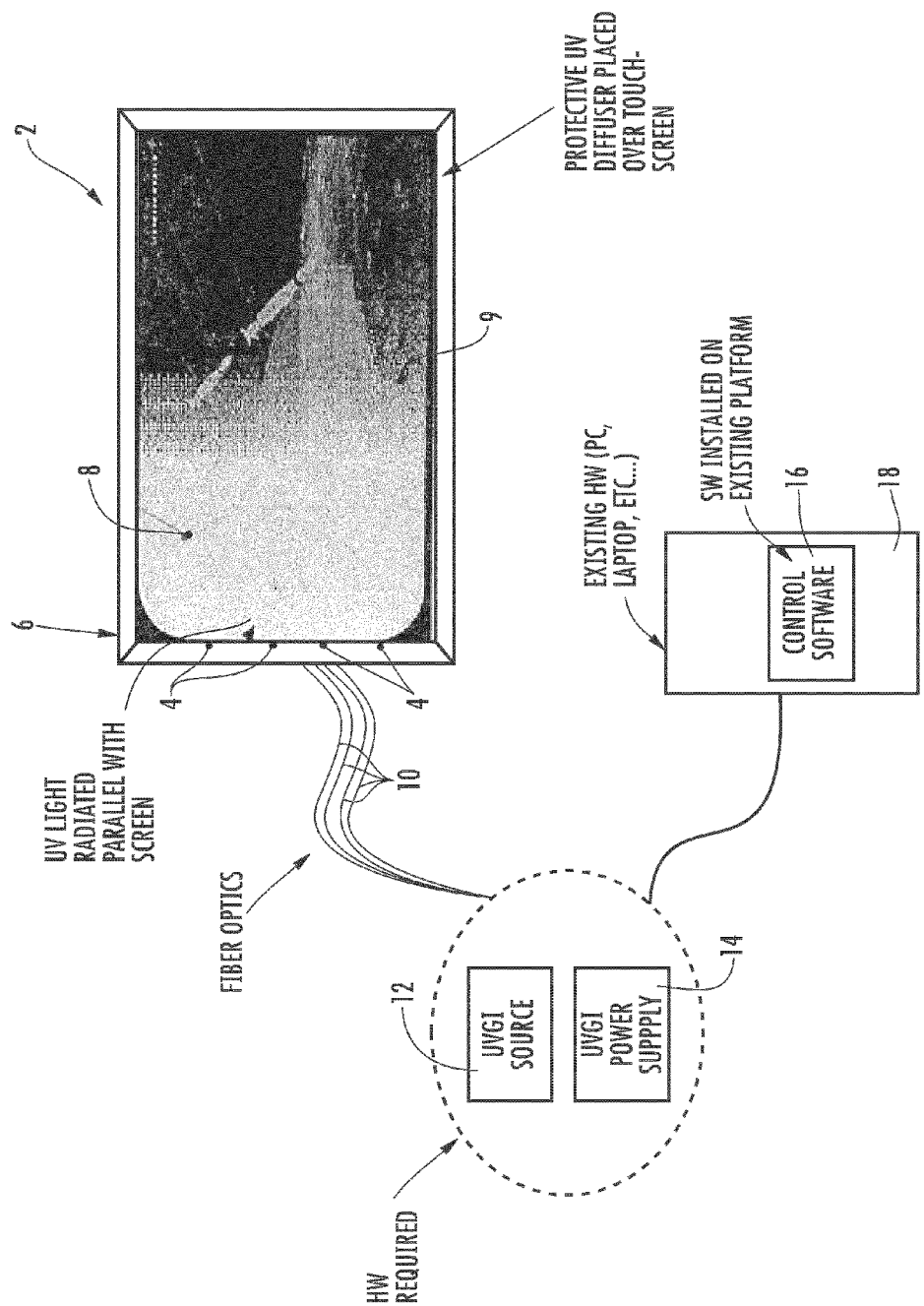
FIG. 2 shows an exemplary schematic of the disclosed system adjacent a touch screen monitor.
Figure 3:
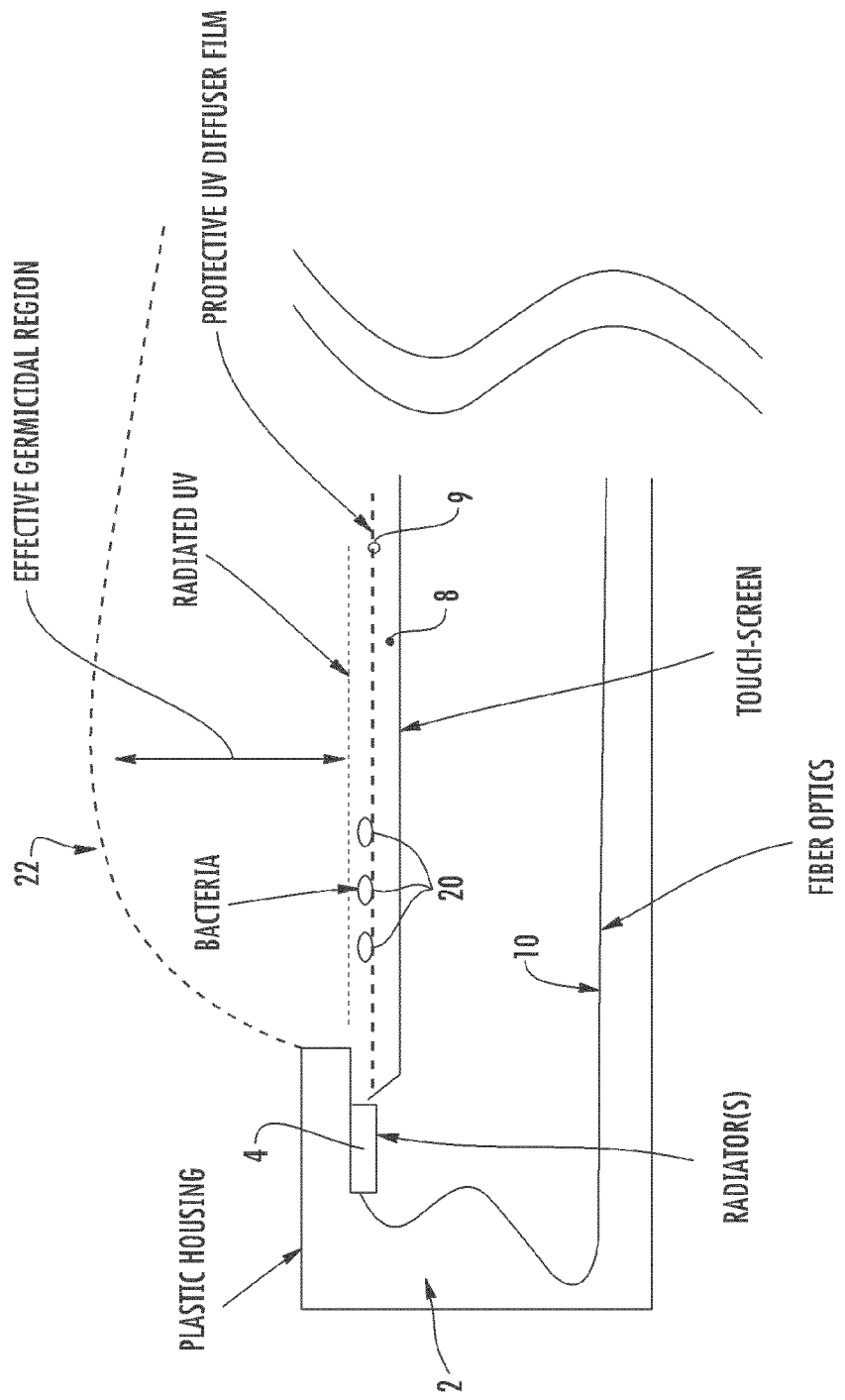
FIG. 3 shows a cross-section view of a portion of the system of FIG. 2.

FIGS. 2 and 3 show the disclosed system incorporated into an exemplary electronic device. Specifically, FIGS. 2 and 3 illustrate the incorporation of the disclosed sanitization system into a touch screen panel, namely, a Combat System Touch screen auto-sterilization system. FIG. 2 shows an exemplary touch screen device 2 having a plurality of UVGI radiators 4 disposed along one edge 6 of the touch screen portion 8 of the touch screen device 2. As illustrated, the radiators 4 are oriented to radiate UVC radiation parallel with the surface of the touch screen portion 8. To protect the sensitive electronics of the touch screen portion 8, a UV diffuser 9 can be disposed above top surface of the touch screen portion 8. The UV diffuser 9 may substantially prevent UV radiation from impinging on the touch screen portion 8.

The UVGI radiators 4 are coupled to a plurality of UV-capable fiber-optic fibers 10. The fibers 10, in turn, are coupled to a UVGI source 12. A UVGI power supply 14 provides the necessary power and regulation to the source 12. The UVGI source 12 and power supply 14 can be controlled by software 16 associated with a computer or processor on board the host electronics 18.

Figure 5:
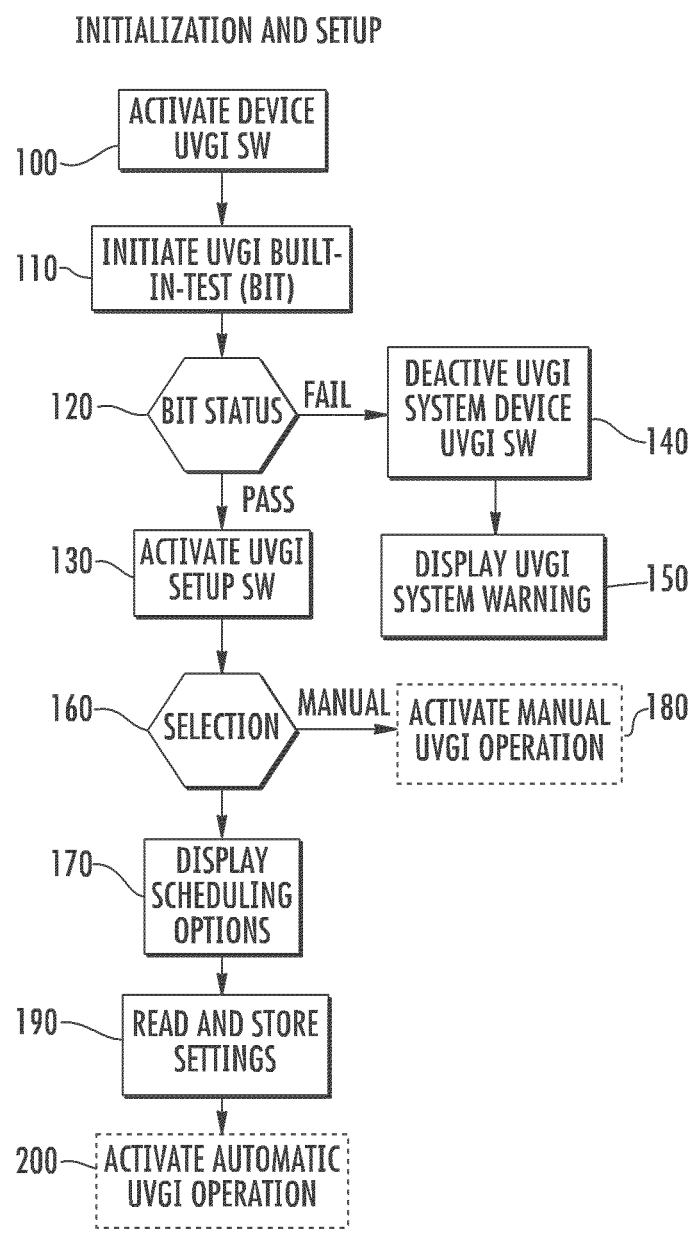
FIG. 5 is a flowchart that illustrates the steps of a first method using the disclosed system.
Figure 6:
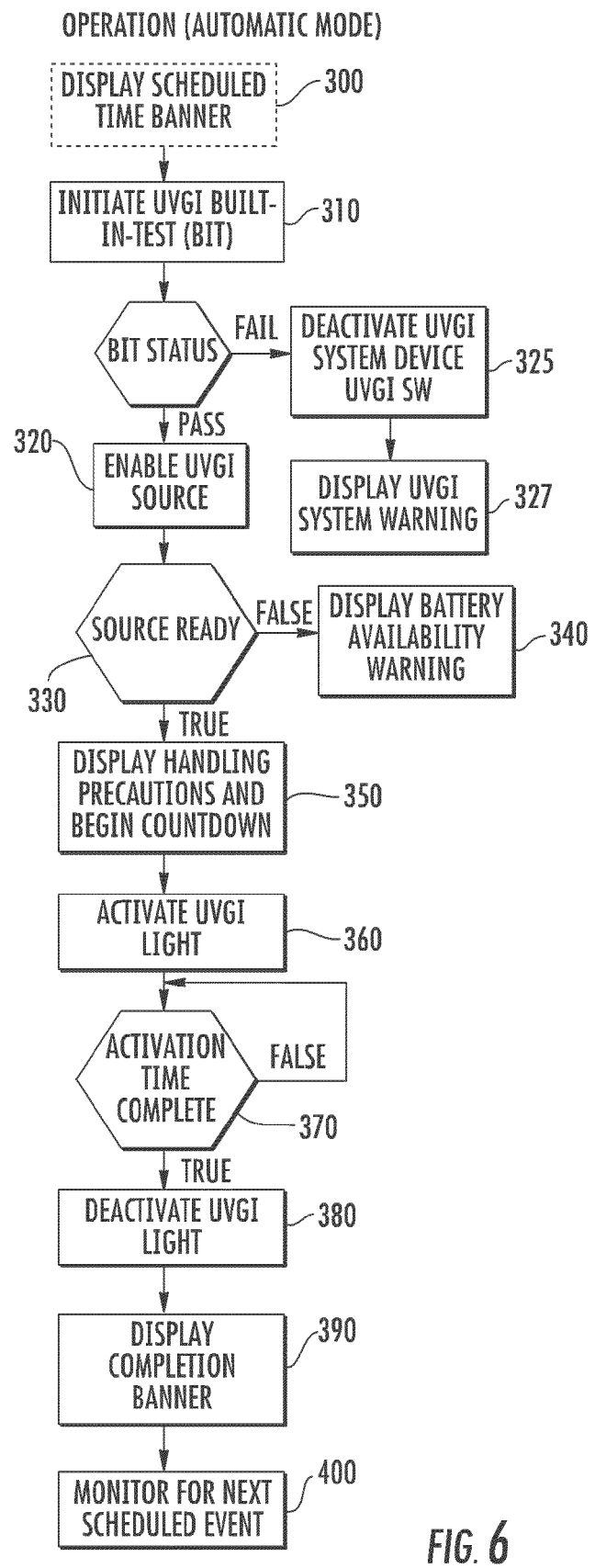
FIG. 6 is a flowchart that illustrates the steps of a second method using the disclosed system.
Figure 7:
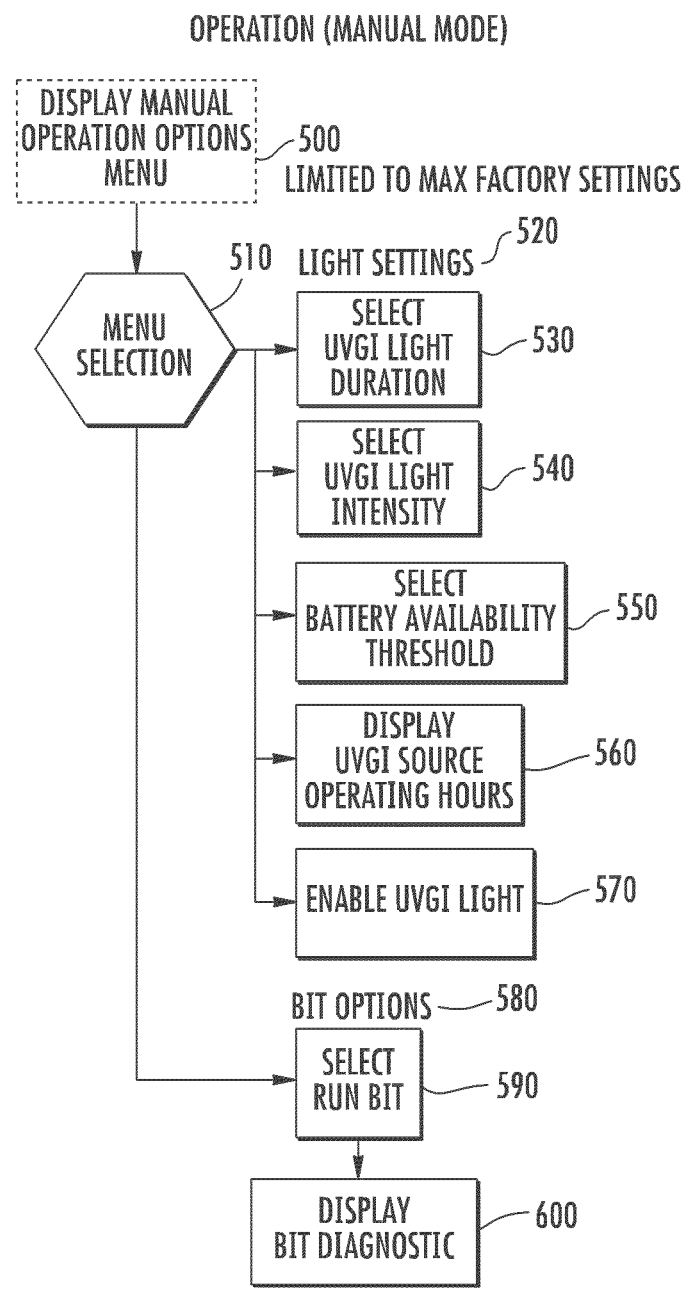
FIG. 7 is a flowchart that illustrates the steps of a third method using the disclosed system.

The software 16 can be customized to manage features such as sterilization scheduling, light intensity, duration, and the like. Careful control of the UVGI source can enhance the effectiveness of the UVGI system. As such the software is setup to allow for dynamic as well as static light management. FIGS. 5-7 are flowcharts illustrating the steps for three exemplary modes of the controlling software 16. The modes are identified as: Initialization and Setup (FIG. 5), Automatic Operation (FIG. 6) and Manual Operation (FIG. 7).

Referring to FIG. 5, Initialization and Setup software is initiated once the UVGI system software has been activated (step 100) (similar to enabling an application on modern smart phones). Once activated the software initiates a Built-In-Test (BIT) (step 110). The BIT ensures that the UVGI system is operating as expected prior to enabling the UVGI light source. Depending on the BIT results (step 120) the software will activate (step 130) or deactivate (step 140) the UVGI system. On a BIT status indicating a failure, the software displays a warning banner and instructions for the user to follow for system maintenance (step 150). A successful BIT will prompt the user (step 160) to enter either the automatic (step 170) or manual (step 180) operation menus. Automatic select will prompt the user to select a maintenance period and time and will be saved to the devices internal memory (step 190). Automatic UVGI operation may then be activated (step 200)

Referring to FIG. 6, Automatic Operation mode allows for the system to self sterilize the touch screen portion 8. Once scheduled sterilization time has been reached (step 300) the system will automatically initiate the BIT function (step 310). With a successful BIT the UVGI source will be enabled (step 320). (If BIT status fails, then the UVGI system device will be deactivated (step 325) and a UVGI system warning will be displayed (step 327).) Enabling of the source will verify, prior to actual radiation, the status of the regulating power supply and/or battery availability (step 330). In the event the inadequate power is available the software will prompt the user of the insufficient battery availability (step 340). With proper battery levels present, the software will display the safe handling guidelines and countdown to UVGI radiation (step 350). The completion of the countdown will trigger the command to turn on the UVGI light (step 360). The light will be active for a preset amount of time (based on the duration needed to effectively sterilize the device) (step 370): Once the sterilization duration has elapsed the UVGI light will be deactivated (step 380) and a completion banner will be displayed (step 390). The system will then return to monitoring for the next scheduled sterilization event (step 400).

Referring to FIG. 7, Manual Operation allows the user to adjust and select various options related to the UVGI light source and the BIT functionality. The selection of the manual operation from the initialization and setup mode (step 500) will prompt a menu selection (step 510). The menu selection is separated in at least two sub-menus. The first, light settings (step 520), allows the user to modify the settings for the UVGI light duration (step 530), light intensity (step 540), battery availability threshold (step 550), and to display UVGI source operating hours (step 560). The light intensity adjustment would be limited to a factory set maximum setting to avoid the risk of excess UVC radiation. Finally, in the light settings menu the option to turn the UVGI light (step 570) on is provided for manual sterilization control. Another feature provided in the software is the ability to access the BIT features (step 580). The option to run a BIT test (step 590) is provided as well as a more detailed diagnostic summary (step 600) is selectable. Both are intended to further allow the user to maintain the system and ensure proper operation.

Referring again to FIG. 3, a cross-section of the FIG. 2 arrangement is shown. The UV-capable fiber optic fibers 10 and the UVGI radiators 4 are shown integrated into the casing of the touch screen device 2. The radiators 4 are positioned to radiate the UVGI radiation substantially parallel to the surface of the touch screen portion 8. The UV diffuser 9 is positioned above the touch screen portion 8 such that the radiated UVGI radiation impinges on the diffuser 9, thereby protecting the touch screen portion 8.

Bacteria 20 residing on the surface of the UV diffuser 9, and within an effective germicidal region 22 will be affected by the UVGI radiation in the manner previously described, thereby sanitizing the surface.

Figure 4:
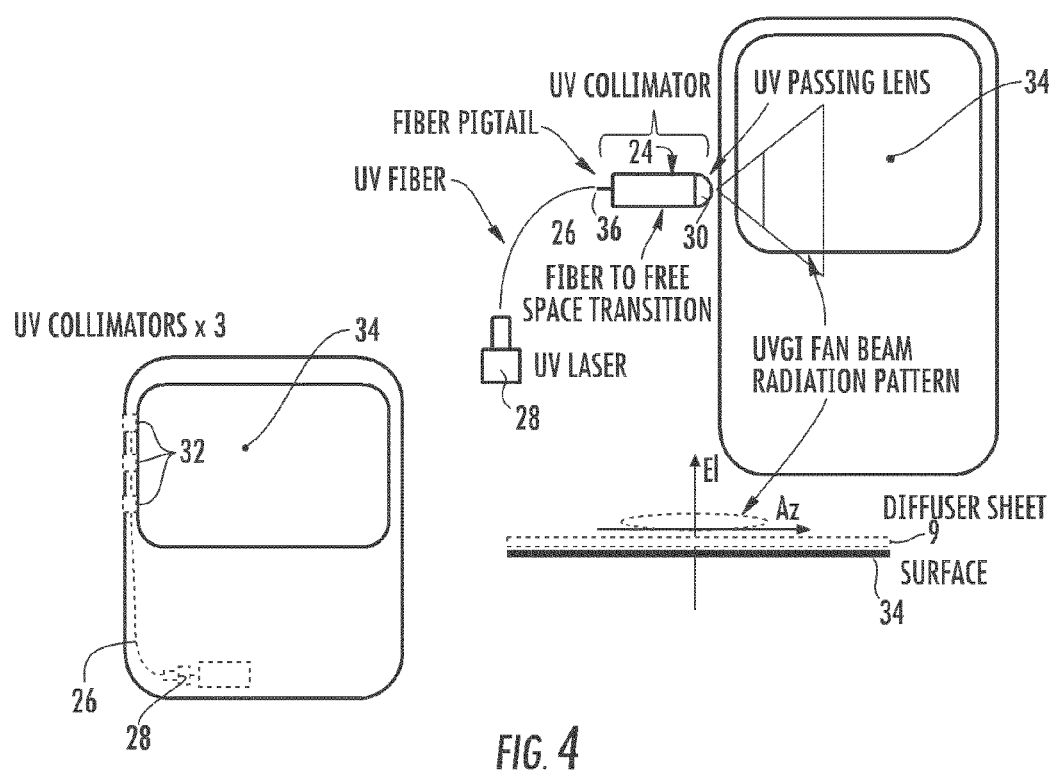
FIG. 4 shows an exemplary arrangement of the disclosed system incorporating a UV laser, fiber and collimator integrated into an electronic device.

The radiators 4 may be a collimator or other UVC radiation method that radiates UVGI radiation in a controlled manner, focusing the beam and preventing it from spilling everywhere. Instead it is desirable that the UVGI radiation be radiated at the surface to be sterilized. Referring to FIG. 4, by utilizing a UV capable collimator 24 and fiber 26 the UVGI light source 28 can be radiated through a lens 30 providing an effective coverage of the sterilizing light. Depending on the size and shape of the device several radiators 32 can be used to ensure the coverage area of the UVGI is such that the full surface to be sterilized receives adequate light to effectively sterilize the surface. The collimator 24 may be comprised of a UV silica lens 30 and UV silica fiber optical termination 36 which accepts the UV fiber feed from the UVGI source. As required, radius bends are applied to the fiber 26 in order to meet the packaging needs the UVGI system is required to have in order to fit within the host device or electronics.

The UV-capable fiber optic fibers 10, 26 can be any of a variety of commercial fibers suitable for the particular application, such as those offered by Polymicro Technologies, LLC, of Phoenix, Ariz. (www.polymicro.com). A small diameter silica based fiber is expected to be used for this application. Bending loss will have to be considered as unique fiber layout is likely needed as the UVGI system is intended to be non-invasive to the host electronics. Likewise, the UVGI diffuser 9 can be a flexible thin film UV filter similar to those offered by Edmund Optics, of Barrington, N.J. (www.edmondoptics.com). The diffuser serves as a means of protecting any UV sensitive electronics contained within the host device.

Due to availability and cost of UVGI sources alternative sources could be utilized. For example UVC capable light emitting diodes (LEDs) can be used as an alternative to minimize costs and impact (weight, heat, etc.) to the host equipment. The placement of the LEDs would be similar to using the radiators for a fiber optic based system. Similarly multiple LEDs would be arranged to provide for full coverage of the surface to be sterilized.

What sets this idea apart from prior methods of sterilizing equipment is that unlike spraying aerosol disinfectant—which requires 10-15 minutes to effectively kill 99.9% of bacteria—UVGI sterilization is achieved within seconds, and with no residue remaining on the equipment. Moreover, some touch screens are made from materials that may be damaged by chemical disinfectants. The disclosed arrangement eliminates the chance of such damage occurring.

With the disclosed arrangement, a device can be sterilized on demand with the need for separate equipment, or the hassle of disconnecting the device and disrupting work. The levels defined for human safety are well above the levels needed to effectively kill bacteria.

The method for operating the disclosed arrangement, as described herein, may be automated by, for example, tangibly embodying a program of instructions upon a computer readable storage media capable of being read by machine capable of executing the instructions. A general purpose computer and/or computer processor is one example of such a machine. A non-limiting exemplary list of appropriate storage media well known in the art would include such devices as a readable or writeable CD, flash memory chips (e.g., thumb drives), various magnetic storage media, and the like.

The features of the system and method have been disclosed, and further variations will be apparent to persons skilled in the art. All such variations are considered to be within the scope of the appended claims. Reference should be made to the appended claims, rather than the foregoing specification, as indicating the true scope of the disclosed method.

The functions and process steps disclosed herein may be performed automatically or wholly or partially in response to user command. An activity (including a step) performed automatically is performed in response to executable instruction or device operation without user direct initiation of the activity.

The disclosed systems and processes are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIGS. 2-4. Further, any of the functions and steps provided in FIGS. 5-7 may be implemented in hardware, software or a combination of both and may reside on one or more processing devices located at any location of a network linking the elements of FIGS. 2-4 or another linked network, including the Internet.

Thus, although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system for sterilizing electronic devices, comprising:
   an ultraviolet (UV) radiation source;
   a distribution fiber coupled to the UV radiation source for transmitting UV radiation to an output end of said distribution fiber;
   a UV collimator coupled to said output end of said distribution fiber; and
   a film positioned on a surface of the electronic device;
   wherein said UV collimator is positioned relative to the film and the electronic device so as to emit UV radiation parallel to the surface of the electronic device and impinge on the film.

2. The system of claim 1, wherein said UV radiation source generates UV radiation at a wavelength in the range of about 2100 Angstroms to about 3100 Angstroms.

3. The system of claim 2, wherein said UV radiation source generates UV radiation at a wavelength of about 2,537 Angstroms.

4. The system of claim 1, wherein said UV radiation source comprises an ultraviolet germicidal irradiation (UVGI) source.

5. The system of claim 1, further comprising a UV power supply coupled to said UV radiation source, wherein said UV power supply, said UV radiation source, said distribution fiber, and a UV radiator coupled to said distribution fiber are all disposed within a casing of said electronic device.

6. The system of claim 1, further comprising a UV power supply coupled to said UV radiation source, and a processor configured to execute instructions for controlling said UV power supply.

7. The system of claim 6, wherein said electronic device is selected from the list consisting of a cellular telephone, a personal digital assistant, a keyboard and a touch screen.

8. The system of claim 1, further comprising a plurality of UV radiation sources coupled to a plurality of distribution fibers for exposing a plurality of surfaces of said electronic device to sterilizing UV radiation.

9. The system of claim 6, wherein said processor is further configured to execute instructions for automatically:
    activating said UV radiation source at a predetermined time;
    maintaining said UV radiation source in an active state for a predetermined duration, and
    deactivating said UV radiation source at the end of the predetermined duration.

10. The system of claim 9, wherein said processor is further configured to execute instructions for performing a test function, said test function verifying the operability of the system prior to the step of activating said UV radiation source.

11. The system of claim 9, wherein said processor is further configured to execute instructions for verifying that the available power from said UV power supply is sufficient for performing the steps of said automatically activating, maintaining and deactivating prior to initiation of said activating step.

12. The system of claim 9, wherein said processor is further configured to output an indication of the completion of the step of deactivating said UV radiation source.

13. The system of claim 6, wherein said processor is responsive to a user-input for adjusting the intensity of the UV radiation output by the UV radiation source.

* * * * *